United States Patent
Liu et al.

(10) Patent No.: US 9,936,882 B2
(45) Date of Patent: Apr. 10, 2018

(54) BLOOD PRESSURE MONITOR COORDINATED WITH A CARDIOVASCULAR HEALTH CONDITION MONITORING MODULE

(71) Applicants: ACME Portable Corp., New Taipei (TW); ACME Portable Machines, Inc., Azusa, CA (US)

(72) Inventors: Changyu Liu, Yuanlin (TW); Yii-Leh Kao, Taipei (TW); Tsair Kao, New Taipei (TW)

(73) Assignees: ACME PORTABLE MACHINES, INC., Azusa, CA (US); ACME PORTABLE CORP., New Taipei (TW)

( * ) Notice: Subject to any disclaimer, the term of this patent is extended or adjusted under 35 U.S.C. 154(b) by 0 days.

(21) Appl. No.: 15/015,757

(22) Filed: Feb. 4, 2016

(65) Prior Publication Data

US 2017/0135585 A1    May 18, 2017

(30) Foreign Application Priority Data

Nov. 13, 2015  (TW) .................................. 104137591

(51) Int. Cl.
  *A61B 5/02*    (2006.01)
  *A61B 5/00*    (2006.01)
  *A61B 5/024*   (2006.01)

(52) U.S. Cl.
  CPC ............. *A61B 5/02* (2013.01); *A61B 5/0059* (2013.01); *A61B 5/02416* (2013.01)

(58) Field of Classification Search
  CPC ........ A61B 5/02416; A61B 5/044; A61B 5/02
  See application file for complete search history.

(56) References Cited

U.S. PATENT DOCUMENTS

| | | | | |
|---|---|---|---|---|
| 5,919,141 A | * | 7/1999 | Money | A61B 5/02055 600/483 |
| 2003/0120164 A1 | * | 6/2003 | Nielsen | A61B 5/02055 600/513 |
| 2007/0167852 A1 | * | 7/2007 | Sugo | A61B 5/029 600/513 |
| 2010/0268518 A1 | * | 10/2010 | Sugo | A61B 5/029 703/2 |
| 2014/0066732 A1 | * | 3/2014 | Addison | A61B 5/029 600/324 |
| 2014/0180136 A1 | * | 6/2014 | Su | A61B 5/7221 600/479 |

OTHER PUBLICATIONS

Notice of Allowance issued in corresponding TW Application No. 104137591 with English translation dated Nov. 15, 2017 (4 pages).

* cited by examiner

*Primary Examiner* — George Evanisko
(74) *Attorney, Agent, or Firm* — Osha Liang LLP

(57) ABSTRACT

A blood pressure monitor equipped with a cardiovascular health condition monitoring module includes: a blood pressure measurement device measuring a user's blood pressure signal; a host including a blood pressure monitor microprocessor that processes blood pressure correlated signal; a control panel equipped to the host and configured to control blood pressure measured by the blood pressure monitor and heart rhythm analysis; a first display device displaying blood pressure result; and a second display device displaying heart rhythm analysis from the cardiovascular health condition monitoring module.

9 Claims, 7 Drawing Sheets

BLOOD PRESSURE MONITOR COORDINATED WITH A CARDIOVASCULAR HEALTH CONDITION MONITORING MODULE

FIELD OF THE INVENTION

The present invention relates to a cardiovascular health condition monitoring module and a blood pressure monitor therewith, particularly relates to a blood pressure monitor coordinated with a cardiovascular health condition monitoring module, which may display detecting result of cardiovascular health from the cardiovascular health condition monitoring module.

BACKGROUND OF THE INVENTION

Blood pressure monitor is common for simplified medical station, so people having cardiovascular disease record can know their own health condition by measuring blood pressure. However, general blood pressure monitor only measures blood pressure variance and there is no other function for general blood pressure monitor. It is necessary for those who have cardiovascular correlated trouble and need to monitor blood pressure to have an apparatus that can measures other cardiovascular correlated parameters for monitoring user's cardiovascular health condition, finding health correlated trouble and notifying user of accepting medical care early. Thus, it is an important issue to develop blood pressure monitor of multitudes functions.

Atrial fibrillation is the most common clinical arrhythmia among cardiovascular correlated diseases. Atrial fibrillation and arrhythmia often happen on people suffering hypertension, cardiac failure, diabetes mellitus or hyperthyroidism diseases or elders. Once atrial fibrillation happens, atrium can not contract to pump blood so as to possibly result in thrombus and stroke. According to statistics, patients of atrial fibrillation disease have five times probability higher than normal people to suffer stroke. For high-risk population suffering cardiovascular correlated diseases, they usually have blood pressure monitor at home, however, stroke risk may be reduced if they have equipment capable of early detection of atrial fibrillation to notify them to early do health examination and care once the equipment detects out any abnormal condition. It will be convenient for patients to have apparatus integrating monitoring of arrhythmia function with a blood pressure monitor.

Heartbeat may reflect important information about personal health. Heart rhythm represents signal of heartbeat interval in a fixed period and reflects heart condition. There are two detection approaches for heart rhythm: optical transmittance measurement and electric signal measurement. The optical transmittance measurement is also called photoplethysmography, which illuminates skin and measures changes in light absorption or reflection for acquisition of heartbeat condition. On the other hand, electric signal measurement has a principle similar to electrocardiogram method, which utilizes a sensor to directly measure electric signal generated from heart beats for examining user's heart rhythm condition. No matter which methods, optical transmittance measurement and electric signal measurement are used, how to process and analyze the detected signal rapidly and precisely is a key for analysis accuracy of psychological signal.

SUMMARY OF THE INVENTION

Accordingly, a blood pressure monitor of the present invention with a rapid and precise signal-processing method, which includes a cardiovascular health condition monitoring module monitoring arrhythmia such as atrial fibrillation to enhance analysis accuracy of data by multitudes of filtration and judgment.

A blood pressure monitor coordinated with a cardiovascular health condition monitoring module includes: a blood pressure measurement device measuring and outputting a user's blood pressure signal; a cardiovascular health condition monitoring module monitoring and outputting a user's heart rhythm signal; a host coupled with the blood pressure measurement device and the cardiovascular health condition monitoring module, and equipped a microprocessor for processing the user's blood pressure signal and the user's heart rhythm signal and acquiring a heart rhythm measurement result; a control panel deposited at one side of the host and configured to couple with and control the blood pressure measurement device and the cardiovascular health condition monitoring module; and a first display device deposited next to the side with the control panel and coupled the microprocessor to display waveform of the heart rhythm measurement result.

In one embodiment, the blood pressure monitor coordinated with a cardiovascular health condition monitoring module further includes a second display device displaying waveform of a blood pressure measurement result.

In one embodiment, the heart rhythm measurement result of the cardiovascular health condition monitoring module is a PhotoPlethysmoGraphy (PPG) signal.

In one embodiment, the cardiovascular health condition monitoring module monitors heart beats by using transmittance measurement method or electric signal measurement.

In one embodiment, the cardiovascular health condition monitoring module monitors high-resolution heartbeat interval (RR interval) signal.

Accordingly, a blood pressure monitor coordinated with a cardiovascular health condition monitoring module includes: a blood pressure measurement device measuring and outputting a user's blood pressure signal; a cardiovascular health condition monitoring module monitoring and outputting a user's heart rhythm signal, and being equipped with a first microprocessor for processing the user's heart rhythm signal; a host coupled with the blood pressure measurement device and the cardiovascular health condition monitoring module, and equipped a second microprocessor for processing the user's blood pressure signal and the user's heart rhythm signal and acquiring a heart rhythm measurement result; a control panel deposited at one side of the host and configured to couple with and control the blood pressure measurement device and the cardiovascular health condition monitoring module; and a first display device deposited next to the side with the control panel and coupled the second microprocessor to display waveform of the heart rhythm measurement result.

For the blood pressure monitor coordinated with a cardiovascular health condition monitoring module, in one embodiment, the user's heartbeat signal is high-resolution heartbeat interval (RR interval) signal.

Accordingly, a cardiovascular health condition monitoring module includes: a light source device providing a light source and illuminating an object; a signal sensing device measuring signal reflected from the object that is illuminated by the light source and outputting a user's heartbeat signal; and a microprocessor storing and executing a calculation process for analyzing the user's heartbeat signal and acquiring heartbeat variation degree through the calculation process, wherein the heartbeat variation degree is compared with a threshold stored in the microprocessor to analyze user's cardiac health condition.

In one embodiment, the user's heartbeat signal is high-resolution heartbeat interval (RR interval) signal.

Accordingly, the cardiovascular health condition monitoring module of the present invention may monitor arrhythmia via accurate heartbeat variation. The blood pressure monitor coordinated with the cardiovascular health condition monitoring module includes the cardiovascular health condition monitoring module to estimate personal health condition through heartbeat correlated signal. The precise degree of estimating health signal may be enhanced with multiple thorough calculation and filtration for signals in the method of diagnosing personal cardiac health condition by monitoring and analyzing heartbeat of the present invention, so that a variety of health information may be read out therewith. Furthermore, the algorithm of the present invention analyzes values such as differences between the median of heartbeat intervals and each heartbeat interval, average of the each heartbeat intervals, standard deviation of each heartbeat intervals and difference between consecutive two heartbeat intervals, and performs rapid calculation without complicate calculation or analysis. Moreover, less obvious abnormal cardiac atrium correlated signal may be detected out by the method of the present invention with its optimization of signal filtration.

The blood pressure monitor including cardiovascular health condition monitoring module that is a cardiovascular monitor with blood pressure measurement and heart rhythm analysis function may be achieved by adding the cardiovascular health condition monitoring module into a traditional home blood pressure monitor, which is convenient for a patient to monitor daily cardiovascular health.

BRIEF DESCRIPTION OF THE DRAWINGS

The present invention will be apparent to those skilled in the art by reading the following description of a preferred embodiment thereof with reference to the drawings, in which.

DETAILED DESCRIPTION OF THE PREFERRED EMBODIMENT

The present invention involves a cardiovascular health condition monitoring module applied to a blood pressure monitor and the blood pressure monitor coordinated with a cardiovascular health condition monitoring module. User's health condition may be estimated with the cardiovascular health condition monitoring module to measure user's heartbeat signal. The basic principles and functions of a blood pressure monitor will not be illustrated herein because they are well known by one of skilled in the art. However, some characteristics of a blood pressure monitor related to the present invention will be illustrated in detailed in the following paragraphs. Besides, in present invention, heartbeat related data such as "heart rhythm" or "heart rate" are used to further distinguish the cardiovascular health condition of user. It is well known by one of skilled in the art that "heart rate" and "heart rhythm" are both heartbeat related data gained by heartbeat that can demonstrate the health condition of heart, and the value of "heart rate" can be calculated by both raw heartbeat data and "heart rhythm". Furthermore, the figures of the present invention will not be drawn with real sizes or ratios and only described schematically.

Figure 1:
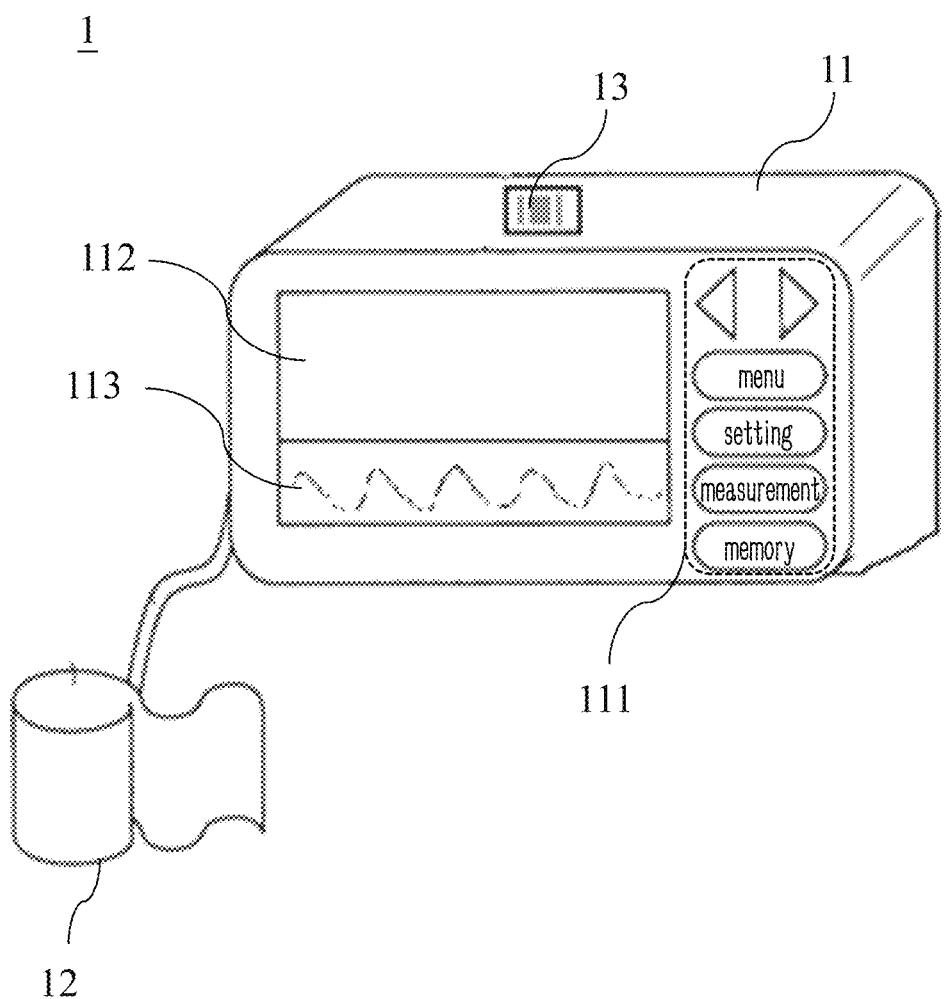
FIG. 1 is a schematic system diagram illustrating a blood pressure monitor according to the present invention.

FIG. 1 is a schematic system diagram illustrating a blood pressure monitor according to the present invention. Please refer to FIG. 1, a blood pressure monitor 1 includes a host 11, a blood pressure measurement device 12 and a cardiovascular health condition monitoring module 13. The host 11 is equipped with a control panel 111 at one side thereof, and it controls and couples to both the blood pressure measurement device 12 and cardiovascular health condition monitoring module 13 with the keys of the control panel 111. Moreover, the host 11 further includes a display device or a feedback device. In one embodiment, the host 11 includes a first display device 112 that is next to the side with the control panel 111 and configured to display measurement result of blood pressure, and a second display device 113 that is next to the side with both the control panel 111 and the first display device 112 and configured to display measurement result and analysis result of heart rhythm. But it is not limited to the ones aforementioned, only display device or multitudes of display or feedback devices may be equipped in the present invention. Furthermore, there may be a microprocessor in the host 11 (not shown in a drawing), and the microprocessor may be the one of blood pressure monitor, the one of cardiovascular health condition monitoring module, or the one of combination thereof, which is not limited in the present invention. In an embodiment, the microprocessor is coupled with the blood pressure measurement device 12 and the cardiovascular health condition monitoring module 13, analyzes blood pressure from the blood pressure measurement device 12 and information processed by the cardiovascular health condition monitoring module 13, and transmits the measured blood pressure signal to the first display device 112 for displaying. Moreover, the microprocessor also receives signal from the cardiovascular health condition monitoring module 13. In an embodiment, the signal of the cardiovascular health condition monitoring module 13 may be transmitted to a display device such as the second display device 113 for displaying, or further processed and then transmitted to a display device for displaying. Those typical or regular components for the host of a blood pressure monitor are well known for one skilled in the art and not be repeated therein. Besides, the blood pressure measurement device 12 may be a pressure cuff, a piezoelectric component device, or an optoelectronic device (photoplethysmography), but it is not limited.

Figure 2:
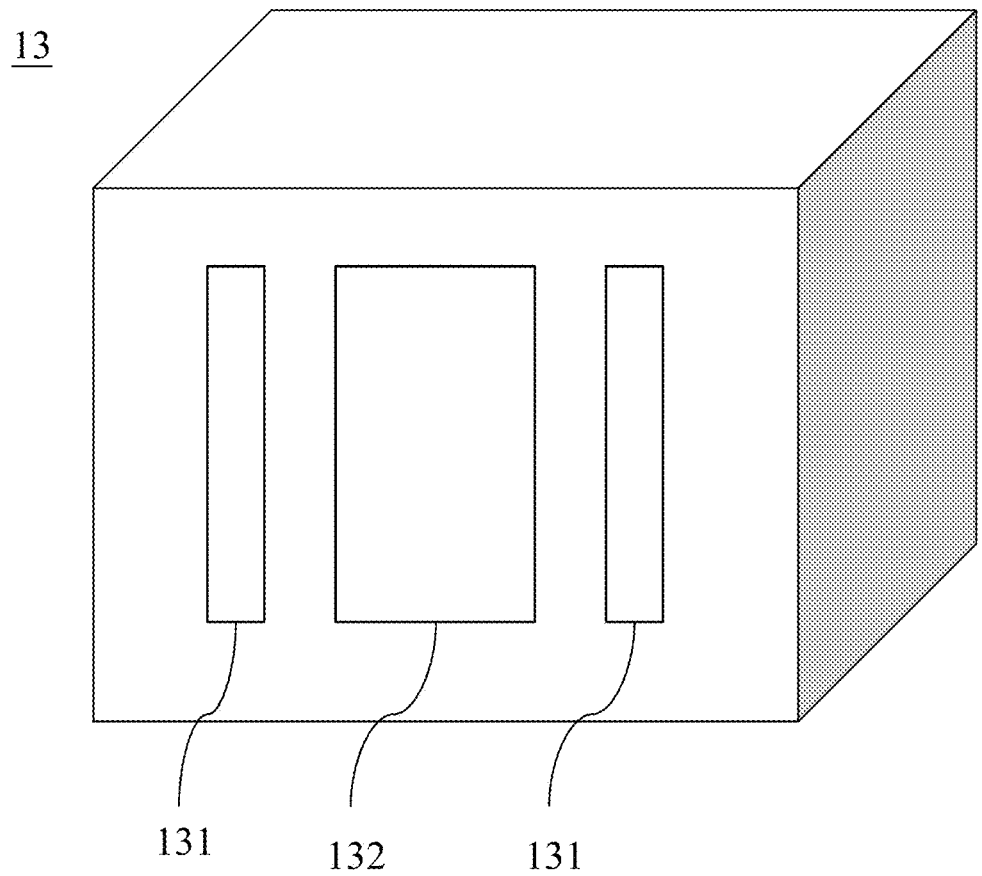
FIG. 2 is a schematic device diagram illustrating a cardiovascular health condition monitoring module according to the present invention.

FIG. 2 is a schematic device diagram illustrating a cardiovascular health condition monitoring module according to the present invention. Please refer to FIG. 2, the cardiovascular health condition monitoring module 13 is a device of monitoring heart beat by using transmittance measurement method that is also called PhotoPlethysmoGraphy (PPG). Moreover, the cardiovascular health condition monitoring module 13 may utilize electric signal measurement to directly measures electric signal generated from contracting cardiac by a sensor, which monitors heartbeat correlated signal or measures the electric signal generated from contracting cardiac to judge user's heart rhythm condition. However, it is not limited to these implement approaches for the cardiovascular health condition monitoring module 13 in the present invention. Please refer to FIG. 2, the cardiovascular health condition monitoring module 13 that utilizes transmittance measurement method includes a light source device 131 and an optical sensor 132. In operation, user may put a finger or an arm onto the cardiovascular health condition monitoring module 13 to touch it with skin. The light source device 131 illuminates user's skin, and the optical sensor 132 receives light signal reflected from or transmitted through user's skin and records its variety for acquisition of cardiac condition. The principle of the cardiovascular health condition monitoring module 13 is based on constant light absorption by skin or muscle tissue at specific zones of human body, but amount of light absorption can be influenced by blood volume within skin. When heart pumps, the blood volume within skin can have pulsation change. When heart contracts, peripheral blood volume is the biggest, so that light absorption is the most, too. Accordingly, when there is a little change in reflected light detected by a light sensor, it is supposed to have one heartbeat. Because there is specific wavelength light absorption for blood, huge amount of light of the specific wavelength emitted from the light source device 131 will be absorbed when heart pumps every time, and heartbeat may be determined by measuring reflected or absorbed light signal. In one embodiment, the microprocessor (not shown in the drawing) in the cardiovascular health condition monitoring module 13 may analyze and process the signal, transmits the analysis result and PPG waveform to the blood pressure monitor microprocessor of the host 11, and further transmits them to the second display device 113 for displaying.

Figure 3:
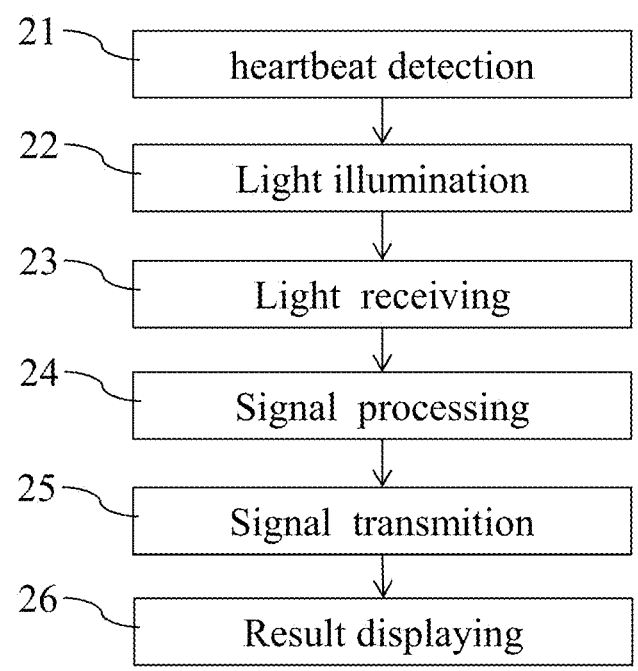
FIG. 3 is a schematic diagram illustrating a flowchart of cardiovascular health condition monitoring module according to the present invention.

FIG. 3 is a schematic diagram illustrating a flowchart of cardiovascular health condition monitoring module according to the present invention. Please refer to FIG. 1 and FIG. 3, the process of the cardiovascular health condition monitoring module 13 includes steps as follows. Function of heartbeat detection is on by user with the control panel 111 on the host 11 of the blood pressure monitor 1 (step 21). At the moment that on state of function of heartbeat detection is ensured, user may put a finger or other body parts onto the cardiovascular health condition monitoring module 13 to touch it with skin for a while. It is not limited to whether user's skin touches onto the light source device 131 and the optical sensor 132 or not. Next, for step 22, the light source device 131 of the cardiovascular health condition monitoring module 13 illuminates user's skin with light beams. Next, for step 23, the optical sensor 132 receives light signal reflected from or transmitted through user's skin. In the embodiment, practical heartbeat signal from the optical sensor 132 may be high-resolution heartbeat interval (RR interval) signal, but it is not limited to in the present invention. Next, step 24, the microprocessor of the cardiovascular health condition monitoring module 13 processes and calculates the received heart rhythm signal in a preset time period, and further outputs an analysis result that may judge whether there is atrial fibrillation. In the embodiment, the cardiovascular health condition monitoring module 13 includes a first microprocessor for processing user's heart rhythm signal. The host 11 includes a second microprocessor, such as a blood-pressure-monitor microprocessor for processing user's blood pressure signal, heart rhythm, and so on. The preset time period is appropriated and fixed, such as 5 seconds, 10 minutes, or between 5 seconds and 10 minutes, but it is not limited to in the present invention. That is, user needs to put the finger or the arm onto the cardiovascular health condition monitoring module 13 for a while. Next, step 25, the cardiovascular health condition monitoring module 13 transmits the analysis result to the blood-pressure-monitor microprocessor of the host 11 in the blood pressure monitor 1. Next, step 26, the blood-pressure-monitor microprocessor of the host 11 outputs the analysis result of the cardiovascular health condition monitoring module 13 to the second display device 113 for displaying. Provided that there is atrial fibrillation during the preset time period in the analysis result of the microprocessor of the cardiovascular health condition monitoring module 13, the diagnostic result such as waveform of cardiac rhythm or atrial fibrillation will be shown on the second display device 113 of the blood pressure monitor 1 for notifying user of caring about self health condition or doing health examination. Moreover, in the embodiment, at the same time of displaying the diagnostic result by the second display device 113, the PPG waveform is also shown on the second display device 113 of the cardiovascular health condition monitoring module 13. The first display device 112 shows blood-associated data measured by the blood pressure measurement device 12.

Figure 4:
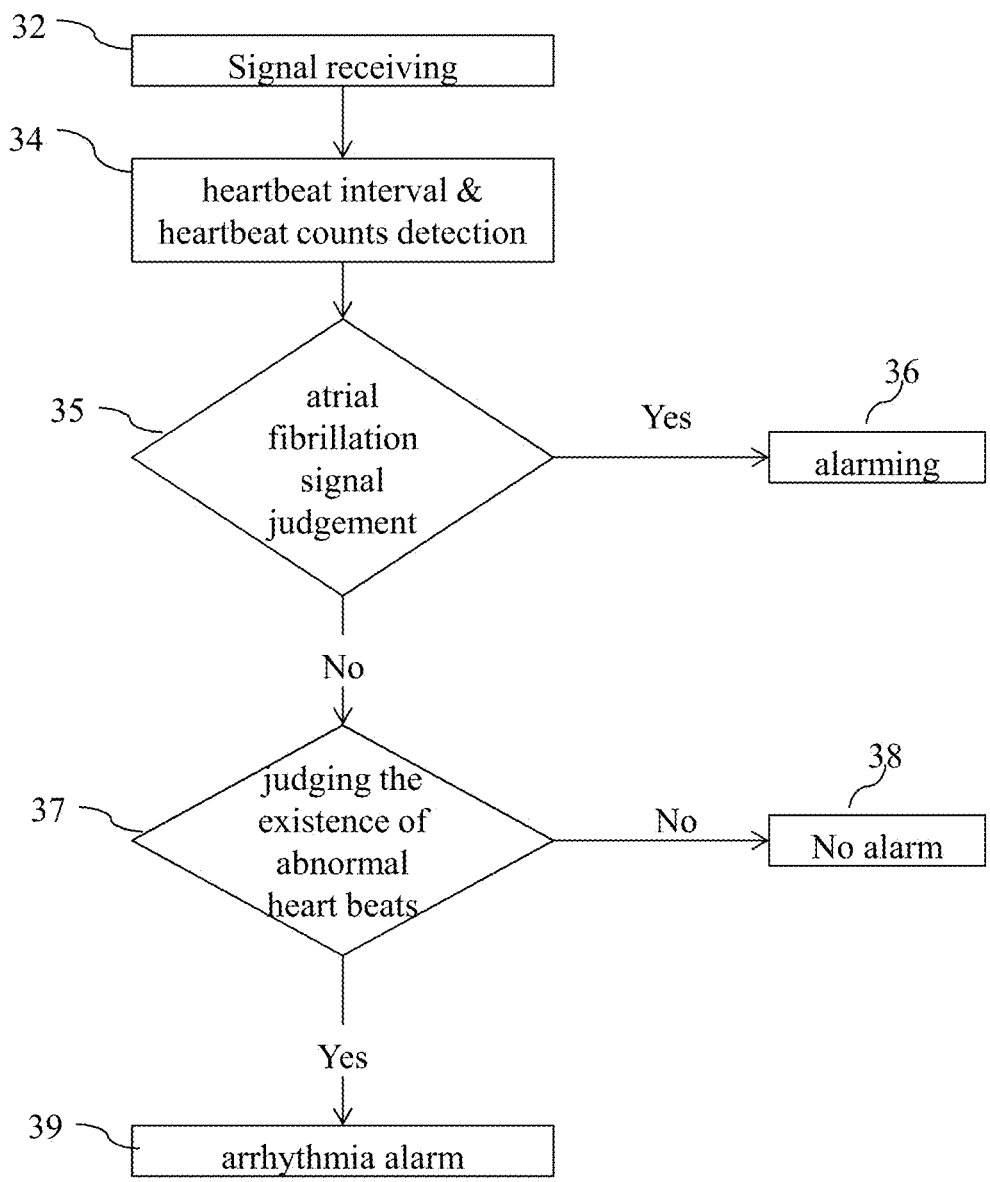
FIG. 4 is a schematic flow diagram illustrating the method of processing personal health signal by heartbeat correlated signal according to the present invention.

Next, FIG. 4 is a schematic flow diagram illustrating the method of processing personal health signal by heart-associated signal according to the present invention. Please refer to FIG. 4, the method of processing personal health signal by heart-associated signal executed by the cardiovascular health condition monitoring module 13 includes the steps as follows. Step 33, heartbeat signal is received. In step 33, the cardiovascular health condition monitoring module 13 monitors user's heartbeat signal. Next, step 34, the cardiovascular health condition monitoring module 13 detects the user's signal of heartbeat interval and the heartbeat counts in the preset interval. In the present invention, the preset time period is appropriated and fixed, such as 5 seconds, 10 minutes, or between 5 seconds and 10 minutes, but it is not limited to in the present invention. Then the cardiovascular health condition monitoring module 13 calculates and judges the signal of heartbeat interval and the heartbeat counts in the preset interval. Next, step 35, whether there is atrial fibrillation signal is judged. With the signal of heartbeat interval, the heartbeat counts, standard deviation, and so on, the microprocessor 14 judges whether the received signal is the one of atrial fibrillation signal. Once there is atrial fibrillation signal, the step 36 will be executed for alarming atrial fibrillation warning. If there is no atrial fibrillation signal, the step 37 will be executed to judge whether there is abnormal heart beat. The abnormal heart beat in the present invention includes premature wave, rapid heartbeat, slow heartbeat, and particular form of heartbeat signal. The normal heart beats are signals derived from sinoatrial node. Step 38 will be executed if there is not abnormal heart beats judged, and no alarm will be sent out. If any abnormal heart beat is judged, it will proceed to step 39 to delivery an arrhythmia alarm. In one embodiment of the present invention, the arrhythmia alarm is shown on the second display device 113. That from step 34 to step 39 are detection steps of heartbeat signal will be illustrated in detail in the following paragraphs.

Figure 5:
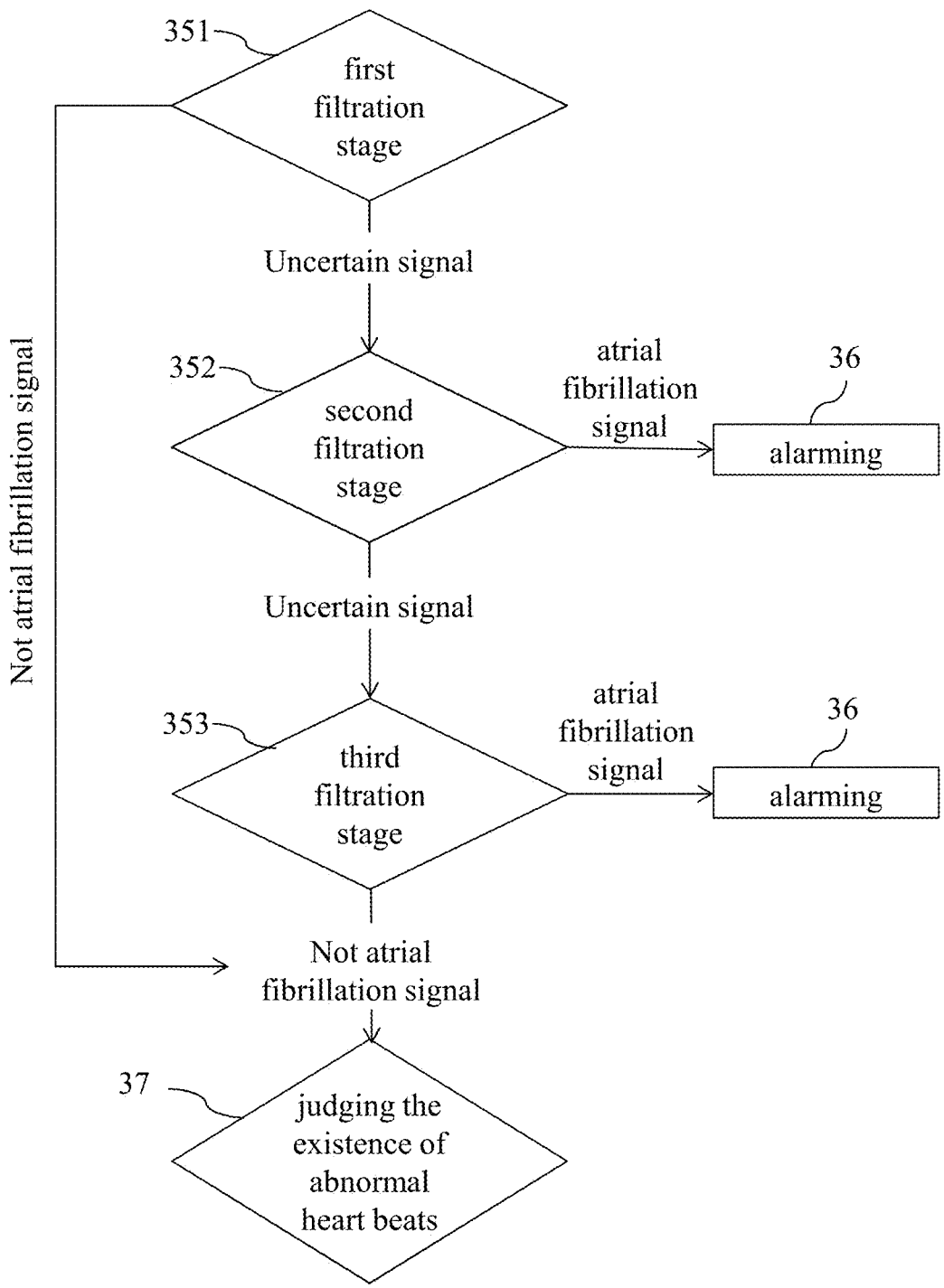
FIG. 5 is a schematic flow diagram illustrating filtration for the detected atrial fibrillation signal according to the present invention.

FIG. 5 is a schematic flow diagram illustrating filtration for the detected atrial fibrillation signal according to the present invention. The detected signal may be judged whether it is atrial fibrillation in step 35. Step 35 includes some signal processing and signal filtration stages. Step 351: that whether the detected signal is non-atrial fibrillation is determined in step 351 of the first filtration stage. If the detected signal is first determined to be non-atrial fibrillation signal in step 351, step 37 for judging existence of the abnormal heartbeats is next executed. If the detected signal is possible atrial fibrillation signal, the process goes into step 352 of the second filtration stage. In step 352, the detected signal that is supposed to be atrial fibrillation in step 351 may be further filtered out to determine whether it is atrial fibrillation and step 36 may be executed for alarming atrial fibrillation. In one embodiment, the atrial fibrillation alarm is shown on the second display device 113. In other embodiments of the present invention, there may be the third filtration stage. After the second filtration stage of screening/excluding out the abnormal heartbeat signal, the process may execute step 353 of the third filtration stage provided that left uncertain signal is over a preset level, such as heartbeat count more than 6 to 10 counts. By passing the third filtration stage, unobvious atrial fibrillation signal may be filtered out and then the process may execute step 36 for alarming the warning of atrial fibrillation. It of course goes into step 37 for judging the existence of abnormal heart beats if it is not atrial fibrillation signal.

Figure 6:
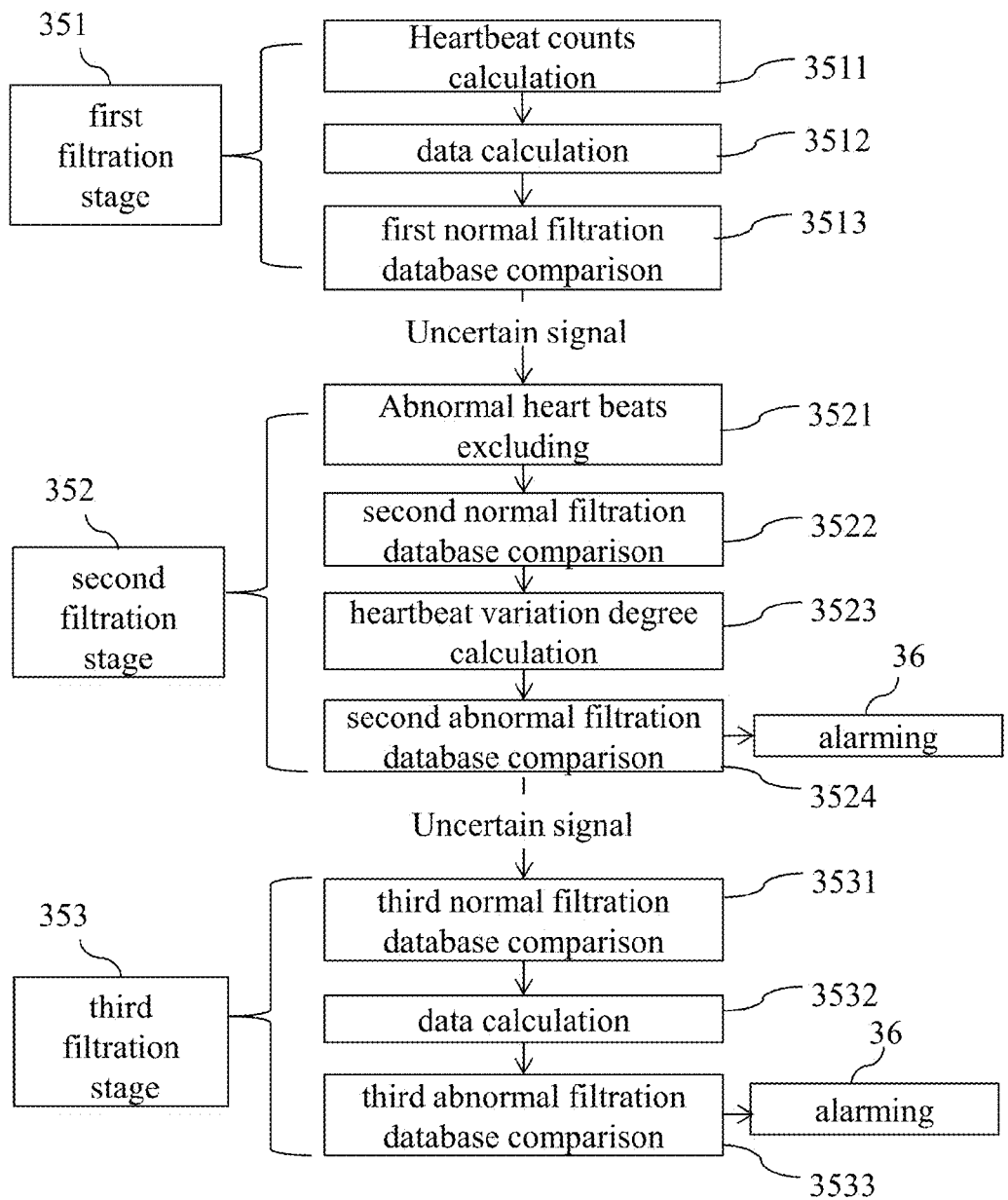
FIG. 6 is a schematic flow diagram illustrating filtration of atrial fibrillation detection signal according to the present invention.

FIG. 6 is a schematic flow diagram illustrating filtration of atrial fibrillation detection signal according to the present invention. Shown in FIG. 6, the detection process of atrial fibrillation includes step 351 of the first filtration stage and step 352 of the second filtration stage. In other embodiments of the present invention, the detection process of atrial fibrillation may include step 353 of the third filtration stage. In these filtration stages, the process can go into step 36 for alarming abnormal atrium on condition that the detected signal is determined to be the atrial fibrillation signal. The details of step 351 of the first filtration stages are illustrated as follows. Heartbeat counts are calculated in a preset time period in step 3511 in which the preset time period is appropriated and fixed, such as 5 seconds, 10 minutes, or between 5 seconds and 10 minutes, but it is not limited to in the present invention. Next, average of all heartbeat intervals, standard deviation, and time differences between the consecutive two heartbeat intervals are calculated in the preset time in step 3512. Next, in step 3513, the detected signal is compared with a first normal filtration database to be determined whether it is non-atrial fibrillation. The first normal filtration database may be one or more judgment rules for statistics of healthy heartbeat trend and include average of normal heart rates, standard deviation of heart rates, and distribution and ratio about difference between consecutive two heart rates, and so on. These values from the first normal filtration database can be compared with the ones in step 3512 to filter out signals met with a range of a normal database. In one embodiment, the first normal filtration database includes a numerical in which the average of heart rate is 80-100 bpm and the standard deviation threshold of heart rate is 20. Compared with the numerical of the first normal filtration database, the detected signal that has 80-100 bpm average value of heart rate and the standard deviation of heart rate smaller than 20 is judged to be the non-atrial fibrillation signal. Then the step 37 goes through to judge whether there is abnormal heart beat. In other embodiment, it is not limited to the numerical in the first normal filtration database has the 10-20 standard deviation threshold of heart rate.

FIG. 6 is a schematic flow diagram illustrating filtration of atrial fibrillation detection signal according to the present invention. Shown in FIG. 6 again, in step 3513 of the judgment of non-atrial fibrillation signal compared with the numerical of the first normal filtration database, if the detected signal is judged to be abnormal, such as the average value of heart rate not between 80 to 100 bpm and the standard deviation of heart rate more than 20, step 352 of the second filtration stage will be executed. The detailed steps of the second filtration stage are illustrated as follows. Abnormal heart beats will be excluded in step 3521. Those abnormal heart beats are excluded by determining whether the differences between the consecutive two heartbeat intervals and median are more than the threshold of abnormal heart beat. However, the left heartbeat signal is still uncertain. The uncertain heartbeat signal is processed as follows. The time interval difference between the consecutive two heart beats is calculated first and then judged whether it is larger than the threshold of abnormal heart beat. In one embodiment, the threshold of abnormal heart beat may be 5-15 bpm, but it is not limited to in the present invention. That heartbeat difference between the consecutive two heart beats is larger than the threshold of abnormal heart beat is judged to be the abnormal heart beat and excluded. Next, step 3522 of comparison with the second normal filtration database judges whether there is atrial fibrillation. In step 3522, the number of left uncertain heart beats after exclusion of the abnormal heart beats are counted and compared with the second normal filtration database. The second normal filtration database means to include threshold of the number of left signals after exclusion of the abnormal heart beats. For example, the number of signals after exclusion of the abnormal heart beats in the second normal filtration database is 6 heart beats. In the embodiments of the present invention, the threshold of the number of left signals after the exclusion of the abnormal heart beats may be 6-10 heartbeat counts, but it is not limited to in the present invention. If the threshold of the number of left signals in the second normal filtration database is set to be 6 heartbeat counts, after step 3521 of exclusion of abnormal heart beats, that the number of the left uncertain signal is less than 6 heartbeat counts is judged to be not atrial fibrillation signal. Oppositely, that the number of the left uncertain signal is more than 6 heartbeat counts will go into step 3523 of detection of heartbeat variation degree. The heartbeat variation degree of the left uncertain signal after the exclusion step of the abnormal heart beats is calculated for subsequent judgment of the left uncertain signal. The calculation approach of the heartbeat variation degree may calculate a ratio of the heart beats having heartbeat differences within the threshold range to the total heart beats. In one embodiment, the threshold range is set to be the heartbeat difference of 10-40 bpm. Next, go to step 3524 of the comparison with the second abnormal filtration database judges whether there is atrial fibrillation. In step 3524, the heartbeat variation degree calculated in step 3523 may be compared with the second abnormal filtration database for judging whether there is atrial fibrillation. The second abnormal filtration database means to include a threshold of the ratio which is the heart beats having the heartbeat differences within the threshold range to the total heart beats. The threshold range of the heartbeat difference is same as the one in step 3523. In one embodiment, the heartbeat difference may be 10-40 bpm and the threshold of the ratio may be 40-60%. That means, that the heart beats with the heartbeat difference of 10-40 bpm has the ratio over 40-60% of the total heart beats are judged to be atrial fibrillation. If atrial fibrillation is read out in step 3524, step 36 will be executed for alarming atrial fibrillation.

Please refer to FIG. 6, in another embodiment, step 353 of the third filtration stage may execute on condition that the judged heartbeat difference is within the threshold range of the heartbeat difference and the ratio of the judged heart beats to the total heart beats is not over the threshold of the ratio of the second abnormal filtration database in step 3524. Less obvious atrial fibrillation signal may be further filtered out in step 353. The detail steps of the third filtration stage are illustrated as follows. That whether there is atrial fibrillation is judged with the third normal filtration database in step 3531. A judgment rule in step 3531 includes utilizing correlation judgment of abnormal heart beat to determine whether consecutive heartbeat intervals of abnormal heart beats have times as much as the ones of normal heart beats. Abnormal signals are supposed to be correlated with normal signals, provided that not only there is multiple relationship between the consecutive heartbeat intervals of abnormal heart beats and the ones of normal heart beats but also the multiple relationship meets with threshold of multiple relationship in statistics. Such the abnormal signals are possible not to be atrial fibrillation ones but needed to be further analyzed. In one embodiment, the threshold of multiple relationships aforementioned may be any values of 1.3 to 2.5 times, but it is not limited to in the present invention. The correlation of abnormal heart beat may reach 50-80% on condition that the threshold of multiple relationships is from 1.3 to 2.5 times. The signal is judged to be atrial fibrillation one if the correlation of abnormal heart beat does not reach 50-80%, and the process will go into step 36 for alarming atrial fibrillation warning. Oppositely, if the multiple relationships between the consecutive heartbeat intervals of abnormal heart beats and the ones of normal heart beats is 1.3 to 2.5 times, it means the correlation of abnormal heart beat reaches 50-80% and the detected signal needs to be analyzed by step 3532 because atrial fibrillation signal is uncertain. Standard deviation of the left heartbeat intervals are calculated in step 3532. That is, the standard deviation of the left heartbeat intervals after the exclusion of the abnormal heart beats in the second filtration stage are calculated for further filtration and judgment. Next, the signal is judged with the third abnormal filtration database to determine whether it is atrial fibrillation in step 3533. Step 3533 may filter less obvious abnormal signals and utilize the third abnormal filtration database of statistics of heartbeat trend for atrial fibrillation individuals. The judgment rules used in the third abnormal filtration database include average of normal heart rate, average of heart rate, standard deviation of heart rate, and distribution and ratio about difference between consecutive two heart rates, and so on. These values from the third abnormal filtration database can be compared with the ones in step 3532 to filter out signals met with atrial fibrillation data. The statistics approach used in the third abnormal filtration database is same as the ones in the first normal filtration database of step 3513 and the second abnormal filtration database of step 3524, but has the smallest numerical range in third abnormal filtration database to more precisely and severely filter out less obvious atrial fibrillation signals. In one embodiment, the third abnormal filtration database includes a numerical that represents standard deviation threshold of normal heart heat. In one embodiment, the standard deviation threshold of normal heart beat is 5-15 bpm, such as 10 bpm. Provided that the standard deviation threshold of normal heart beat is 10 bpm, a value of more than 10 bpm calculated in step 3532 is judged to be atrial fibrillation and then step 36 may be executed for alarming atrial fibrillation warning.

Figure 7:
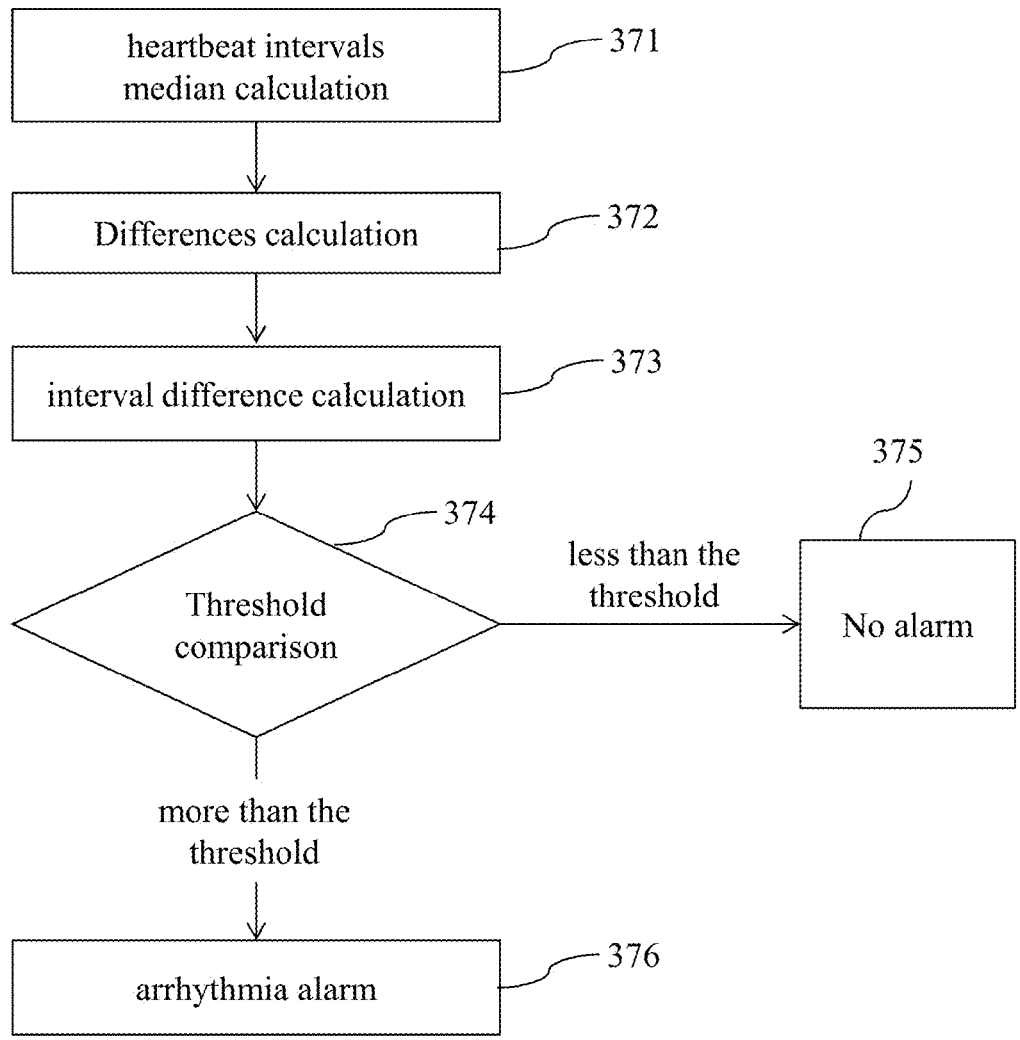
FIG. 7 is a schematic flow diagram illustrating detection of abnormal heart beats according to the present invention.

FIG. 7 is a schematic flow diagram illustrating detection of abnormal heart beats according to the present invention. Shown in FIG. 7, step 37 of judgment of abnormal heart beat includes: median of all heartbeat intervals in a preset time intervals is calculated in step 371. Differences between the median of all heartbeat intervals and the all heartbeat intervals are calculated in step 372. Optionally, interval difference between consecutive heart beats is calculated in step 373 for more precise judgment. Next, that whether difference between the median of all heartbeat intervals and each heartbeat interval is more than the threshold of abnormal heart beat is judged in step 374. In one embodiment, the threshold of abnormal heart beat may be 5-15 bpm, but it is not limited to in the present invention. If the difference between the median of all heartbeat intervals and each heartbeat interval is less than the threshold of abnormal heart beat of 5-15 bpm, there is no abnormal heart beats and step 375 does not execute alarm. Provided that the difference between the median of all heartbeat intervals and each heartbeat interval is more than the threshold of abnormal heart beat of 5-15 bpm, step 376 will be executed to alarm arrhythmia for existence of abnormal heart beat. In one embodiment, the arrhythmia alarm is shown on the second display device 113, but other display approaches such as acoustic alarm are allowed in other embodiments.

In another embodiment, the method of estimating personal health condition by monitoring heartbeat correlated signals executed by cardiovascular health condition monitoring module 13 further includes step of symptom analysis (not shown in drawings) after the detection step of abnormal heart beat to make precise analysis on heartbeat information. The step of symptom analysis may determine physiological conditions with respect to heart beats, such as arrhythmia, and be executed on the condition of no atrial fibrillation signal. The step of symptom analysis includes: by utilizing rhythm algorithm program, the microprocessor 14 judges positions of abnormal heart beats in the signal of heartbeat intervals. For example, there are 10 waves in whole signal and the second wave is detected to have abnormal heart beat, so the position with respect to the abnormal heart beat is 2. The memory 13 stores information of possible symptoms with respect to each position of abnormal heart beat. The rhythm algorithm program may analyze the detected positions of abnormal heart beats and compare them with data in a database to further determine how the detected position is corresponded to symptom and whether there is premature wave, rapid heartbeat, slow heartbeat, or special rhythm. For example, that there are more than twice intervals between abnormal and normal heart beats will be judged to be double rhythm. Then symptom signal is transmitted to the feedback module 15, such as a display, after the acquisition of analysis result. In one embodiment, the display is the second display device 113.

In the embodiments of the present invention, a cardiovascular monitor with blood pressure measurement and heart rhythm analysis function may be achieved by adding the cardiovascular health condition monitoring module into a traditional home blood pressure monitor, which is convenient for a patient to monitor daily cardiovascular health.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A blood pressure monitor coordinated with a cardiovascular health condition monitoring module, comprising:
a blood pressure measurement device that measures and outputs a user's blood pressure signal;
a cardiovascular health condition monitoring module comprising a light source device and an optical sensor, wherein the cardiovascular health condition monitoring module detects a heartbeat interval signal of the user, obtains a heart rhythm signal by the heartbeat interval signal, and outputs the heart rhythm signal of the user;
a host coupled with the blood pressure measurement device and the cardiovascular health condition monitoring module, the host equipped with a microprocessor that processes the user's blood pressure signal and the user's heart rhythm signal, and that acquires a waveform of a heart rhythm measurement result from the user's heart rhythm signal;
a control panel deposited at one side of the host and configured to couple with and control the blood pressure measurement device and the cardiovascular health condition monitoring module; and
a first display device deposited next to the side with the control panel and coupled to the microprocessor to display whether the waveform of the heart rhythm measurement result is an atrial fibrillation signal,
wherein the processing of the user's blood pressure signal and the user's heart rhythm signal by the host comprises:
a first filtration stage comprising calculating an average of all heartbeat intervals, a standard deviation of all the heartbeat intervals, and differences between two consecutive heartbeat intervals according to the heartbeat interval signal to determine whether there is the atrial fibrillation signal; and
a second filtration stage comprising excluding abnormal heartbeat signals by determining the differences between the two consecutive heartbeat intervals and a median of all the heartbeat intervals so as to determine whether there is the atrial fibrillation signal, when the first filtration stage is not able to determine whether there is the atrial fibrillation signal.

2. The blood pressure monitor coordinated with the cardiovascular health condition monitoring module of claim 1, further comprising:
a second display device,
wherein the microprocessor acquires a waveform of a blood pressure measurement result from the user's blood pressure signal, and
wherein the second display device displays the waveform of the blood pressure measurement result.

3. The blood pressure monitor coordinated with the cardiovascular health condition monitoring module of claim 1, wherein the waveform of the heart rhythm measurement result of the cardiovascular health condition monitoring module is a PhotoPlethysmoGraphy (PPG) waveform.

4. The blood pressure monitor coordinated with the cardiovascular health condition monitoring module of claim 1, wherein the cardiovascular health condition monitoring module monitors heartbeats by using a transmittance measurement to detect and output the user's heart rhythm signal.

5. The blood pressure monitor coordinated with the cardiovascular health condition monitoring module of claim 1, wherein the processing of the user's blood pressure signal and the user's heart rhythm signal by the host further comprises:
a third filtration stage comprising calculating a standard deviation of remaining heartbeat intervals, the remaining heartbeat intervals being the heartbeat intervals that remain after the abnormal heartbeat signals are excluded during the second filtration stage, and determining whether there is the atrial fibrillation signal by comparing the standard deviation of the remaining heartbeat intervals with a third abnormal filtration database, when the second filtration stage is not able to determine whether there is the atrial fibrillation signal,
wherein the third abnormal filtration database uses judgment rules comprising average of normal heart rate, average heart rate, standard deviation of heart rate, and distribution and ratio about difference between two consecutive heart rates.

6. A blood pressure monitor coordinated with a cardiovascular health condition monitoring module, comprising:
a blood pressure measurement device that measures and outputs a user's blood pressure signal;
a cardiovascular health condition monitoring module that detects a heartbeat interval signal of the user, obtains a heart rhythm signal by the heartbeat interval signal, and outputs the heart rhythm signal of the user, the cardiovascular health condition monitoring module being equipped with a light source device, an optical sensor, and a first microprocessor that processes the user's heart rhythm signal;
a host coupled with the blood pressure measurement device and the cardiovascular health condition monitoring module, the host equipped with a second microprocessor that processes the user's blood pressure signal and the user's heart rhythm signal, and that acquires a waveform of a heart rhythm measurement result from the user's heart rhythm signal;
a control panel deposited at one side of the host and configured to couple with and control the blood pressure measurement device and the cardiovascular health condition monitoring module; and
a first display device deposited next to the side with the control panel and coupled to the second microprocessor to display whether the waveform of the heart rhythm measurement result is an atrial fibrillation signal,
wherein the processing of the user's blood pressure signal and the user's heart rhythm signal by the host comprises:
a first filtration stage comprising calculating an average of all heartbeat intervals, a standard deviation of all the heartbeat intervals, and differences between two consecutive heartbeat intervals according to the heartbeat interval signal to determine whether there is the atrial fibrillation signal; and
a second filtration stage comprising excluding abnormal heartbeat signals by determining the differences between the two consecutive heartbeat intervals and a median of all the heartbeat intervals so as to determine whether there is the atrial fibrillation signal, when the first filtration stage is not able to determine whether there is the atrial fibrillation signal.

7. The blood pressure monitor coordinated with the cardiovascular health condition monitoring module of claim 6, further comprising:
a second display device, wherein the second microprocessor acquires a waveform of a blood pressure measurement result from the user's blood pressure signal, and wherein the second display device displays the waveform of the blood pressure measurement result.

8. The blood pressure monitor coordinated with the cardiovascular health condition monitoring module of claim 6, wherein the user's heart rhythm signal is a beat-beat interval signal that is output by the optical sensor of the cardiovascular health condition monitoring module to the first microprocessor of the cardiovascular health condition monitoring module.

9. The blood pressure monitor coordinated with the cardiovascular health condition monitoring module of claim 6, wherein the processing of the user's blood pressure signal and the user's heart rhythm signal by the host further comprises:

a third filtration stage comprising calculating a standard deviation of remaining heartbeat intervals, the remaining heartbeat intervals being the heartbeat intervals that remain after the abnormal heartbeat signals are excluded during the second filtration stage, and determining whether there is the atrial fibrillation signal by comparing the standard deviation of the remaining heartbeat intervals with a third abnormal filtration database, when the second filtration stage is not able to determine whether there is the atrial fibrillation signal, wherein the third abnormal filtration database uses judgment rules comprising average of normal heart rate, average heart rate, standard deviation of heart rate, and distribution and ratio about difference between two consecutive heart rates.

\* \* \* \* \*